United States Patent [19]

Deininger et al.

[11] 4,158,006
[45] Jun. 12, 1979

[54] REFINING SACCHARIN SODIUM

[75] Inventors: Rolf Deininger, Cologne; Erich Wolf, Marialinden, both of Fed. Rep. of Germany

[73] Assignee: Chimicasa GmbH, Chur, Switzerland

[21] Appl. No.: 819,255

[22] Filed: Jul. 27, 1977

[30] Foreign Application Priority Data

Aug. 2, 1976 [LU] Luxembourg .......................... 75518

[51] Int. Cl.² .......................................... C07D 275/06
[52] U.S. Cl. .................................... 260/301; 426/548
[58] Field of Search ........................................ 260/301

[56] References Cited
U.S. PATENT DOCUMENTS 3,988,344 10/1976 Nakaoji ............................... 260/301

OTHER PUBLICATIONS

*The Condensed Chemical Dictionary*, Eighth Edition, VanNostrand Reinhold, N.Y., 1971, pp. 572–573.
Weissberger (ed.) *Technique of Organic Chemistry*, vol. III, (2nd Ed.), Part I, Interscience, N.Y., 1956, pp. 301–302.

*Primary Examiner*—Paul M. Coughlan, Jr.
*Attorney, Agent, or Firm*—Kane, Dalsimer, Kane, Sullivan and Kurucz

[57] ABSTRACT

The disclosure is of a process for refining crude saccharin sodium (saccharin soluble) to remove organic contaminants. The process comprises extraction of an acid solution of the crude saccharin sodium, using methylene chloride to extract the contaminants.

5 Claims, 1 Drawing Figure

REFINING SACCHARIN SODIUM

BACKGROUND OF THE INVENTION

1. Field of the Invention

The invention relates to a process for refining crude saccharin sodium (saccharin soluble), contaminated with organic compounds.

2. Brief Description of the Prior Art

The synthesis of saccharin sodium is well known; see for example the method of Fahlberg and Remsen, Chem. Ber., 12, 469 (1879) and U.S. Pat. No. 319,082 (1885). In the latter methods, toluene and chlorosulfonic acid react at 0°–5° C. to form a mixture of o- and p- toluenesulfonamides. The mixture is separated and the o-toluenesulfonamide oxidized to o-carboxybenzenesulfonamide which upon loss of a mole of water forms saccharin in a crude yield. The yield is crude in that it is generally contaminated with by-product organic compounds, principally the unoxidized intermediate o-toluenesulfonamide compound. Attempts have heretofore been made to selectively react the organic contaminant compounds to facilitate their separation from the saccharin sodium by conventional precipitation or crystallization. However, the desired purity level is generally not achieved and the methods are costly to carry out.

The impurities or contaminants of concern obtained in admixture with the desired saccharin sodium prepared by the Fahlberg et al. method are largely water-soluble organic compounds. o-toluenesulfonamide is the preponderate impurity and is a contaminant when the saccharin sodium is to be used as a foodstuff because of its toxicity.

We have found that the organic compound contaminants associated with crude saccharin sodium produced by the Fahlberg et al. method are also highly soluble in methylene chloride. Saccharin sodium is substantially insoluble in methylene chloride but is of course readily soluble in water. On the other hand, methylene chloride is soluble only to a very limited degree in aqueous solutions of saccharin sodium and of course water is soluble to only a slight degree in methylene chloride. Thus, the method of our invention yields a refined saccharin sodium, from which the organic contaminants are readily separated. If methylene chloride is present at all in the refined, concentrated and crystallized saccharin sodium, it is only in quantities of less than 1 part per million.

The process of the invention provides a means for the removal of contaminants, resulting in a high purity level for the saccharin sodium while permitting the process to be performed in an economic manner and on an industrial scale.

SUMMARY OF THE INVENTION

The invention comprises a method of refining saccharin sodium to remove organic contaminant compounds, which comprises; extracting the organic contaminant compounds from a solution of the contaminated saccharin sodium, with methylene chloride.

DETAILED DESCRIPTION OF THE PREFERRED EMBODIMENTS OF THE INVENTION

Figure 1:
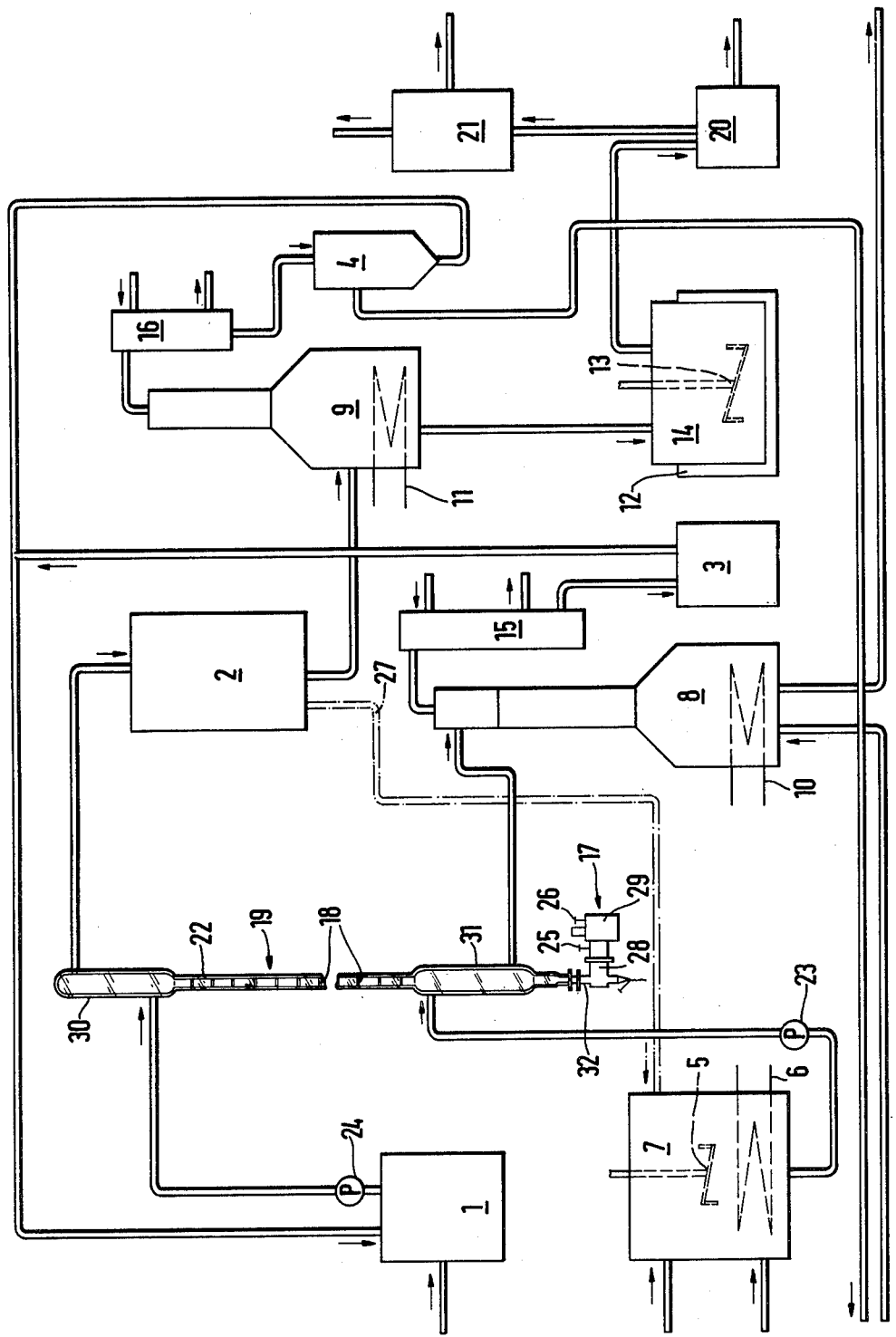
FIG. 1 is a flow diagram depicting a preferred embodiment process of the invention.

The process of the invention may be carried out by extracting an aqueous solution of the crude or unrefined saccharin sodium with methylene chloride, the pH of the aqueous solution being within the range of from 4.5 to 6.0, preferably 5.0 to 5.5. The crude solution may comprise from 30 to 60 percent by crystal weight (preferably 40 percent) of the saccharin sodium to be refined.

The process of the invention may be used to refine crude, crystallized saccharin sodium by first dissolving the crude composition in water to form a solution of the crude composition. For the purpose of forming the solution, water from which the salt has been removed is preferably used and then an acid such as hydrochloric acid and the like is employed to adjust the pH value to the desired range.

Preferably, the process of the invention is carried out on crude saccharin sodium prepared by the aforementioned Fahlberg et al. method. It is in that case advantageous to carry out the process of the invention on the aqueous solution of the crude saccharin sodium product obtained per se in the Fahlberg et al. method, without first crystallizing the saccharin sodium. One need only adjust the concentration and pH of the solution to desired ranges before extracting contaminants. It is then unnecessary to first crystallize the crude aqueous saccharin sodium solution obtained according to the Fahlberg et al process and the saccharin sodium purified according to the process of this invention only has to be crystallized after refinement.

The process according to the invention can also be used on crude saccharin sodium prepared by other known processes, for example by the well known Maume process.

In the preferred process of the invention, extraction of the organic compound contaminants is characterized by the use of methylene chloride in a vertically oriented, countercurrent extraction of a 30 to 60 percent and preferably 40 percent aqueous solution of crude saccharin sodium, adjusted to a pH of 4.5 to 6.0 and preferably a pH of 5.0 to 5.5, wherein the percentages are based on the crystal weight. In such a preferred embodiment, the countercurrent extraction is repeated or continued until the saccharin sodium product crystallizable from the aqueous solution has a content of less than 1 ppm of organic compound impurities. This can be verified by periodic analysis of the aqueous phase of the solution for organic contaminants, after it passes countercurrently with the methylene chloride.

Countercurrent extraction of the participating liquids is advantageously performed at a temperature of from 15° to 22° C., preferably 20° C.

The rate of flow of the methylene chloride compared with that of the crude saccharin sodium solution, which is optimum as regards yield, cost and purity level depends on the concentration of impurities in the crude solution. Generally, a rate of flow of the methylene chloride is advantageously 2 to 3 times that of the crude containing solution. In the case of a 40% crude saccharin sodium solution, preferably the rate of flow of methylene chloride is 2.5 times the rate of flow of the crude containing solution.

Countercurrent extraction may be performed in stages in a plurality of extraction columns arranged in series. However, capitol costs of apparatus is reduced if a single extraction column is used. If a single continuously operating extraction column does not suffice, then the crude saccharin sodium solution and methylene chloride can undergo continuous countercurrent extraction in a closed circuit. It is also possible to adapt a continuous flow of the crude saccharin sodium solution whereby only the methylene chloride is constantly recirculated through the same extraction column on a closed circuit principle. If the methylene chloride flows in a closed circuit, it is recommended that during the return flow it be purified by distillation before re-establishing contact with the crude saccharin sodium solution, whereby it is then particularly suitable for exhaustive extraction. Distillation purification can take place every cycle or every nth cycle using ortho toluene sulphonamide as a function to determine the degree of saturation of the methylene chloride with contaminants.

Under certain circumstances, methylene chloride may contain acid impurities. To keep these away from the counter-current extraction process, it is recommended that 0.2 to 1.0% and preferably 0.5% of potassium carbonate be added to the methylene chloride during distillation. The potassium carbonate bonds the acid impurities so that they cannot pass into the distillate.

For use on an industrial scale, very intense stirring and agitation of the liquids undergoing countercurrent extraction is desired and according to a further development of the process of the invention, this is obtained through emulsifying the liquids which pass one another in counter-current extraction. This is accomplished by circulating them in pulsating or intermittent manner through flow baffle plates, preferably a sieve or packing material placed in the counter flow. The pulsation rate is preferably 100 to 200 pulsation oscillations per minute. The optimum pulsation frequency and amplitude can easily be determined by trial and error, visually observing for example through the glass wall of an extraction column, the droplet structure formed on the baffle plates and then adjusting the frequency and amplitude until a uniform fine droplet distribution is obtained. Account should also be taken of the fact that under certain circumstances a state of equilibrium is not obtained until after 1 to 2 hours of running the extraction column have elapsed.

The invention is explained in greater detail with reference to the attached drawing of FIG. 1 which shows a flow diagram for performing a preferred embodiment process of the invention.

As shown in FIG. 1, the apparatus comprises three storage tanks 1, 2, 3, a separating tank 4, an adjusting tank 7 equipped with a stirrer 5 and a heater 6, two evaporators 8 and 9 with heaters 10, 11, a crystallization tank 14 provided with a cooling jacket 12 and a stirrer 13, two condensers 15, 16 an extraction column 19 equipped with a pulsator 17 and sieve plates 18 serving as flow baffle plates, a separator 20, a drier 21 and two metering pumps 23, 24.

The extraction column 19 comprises an approximately 7 m long vertically positioned glass tube 22, over the length of which and at right angles to the flow are fitted seventy sieve plates 18. The internal cross-section of the glass tube is circular and the diameter is 225 mm. At both the top and bottom the glass tube 22 issues into a separating vessel 30, 31. To the bottom of the lower separating vessel 31 is flanged a connection 32, into which issues the delivery side of a bellows type pump 28 which is driven in pulsating manner by an eccentric drive 29. The pulsation frequency can be adjusted to between 100 and 200 pulsations per minute by means of handle 25. The lift of the bellows type pump 28 can be adjusted to between 20 and 300 cc by means of handle 26. As a result of the action of bellows type pump 28, a pulsating action is exerted on the liquid column in glass tube 22 and the components thereof are consequently driven in pulsating manner through the sieve plates 18 and are thereby emulsified. The sought after purification action is aided by a very intense emulsifying action on the liquids. The optimum setting of the pulsation amplitude and pulsation frequency using handles 25 and 26 is obtained by trial and error. For the operation described hereinafter, the selective settings were 150 pulsations per minute and a pump lift of 40 cc. The remaining parts of the apparatus are dimensioned in accordance with the operating procedure described hereinafter.

The adjusting tank 7 is filled with an aqueous solution of crude saccharin sodium obtained during the synthesis of saccharin sodium according to the Fahlberg-Remsen process, supra. The tank content is adjusted to a pH of 5 by adding hydrochloric acid accompanied by constant stirring by stirrer 5. The temperature of the tank 7 content is adjusted to 20° C. by means of heater 6. The content of adjusting tank 7 is constantly topped up and is continuously readjusted to a pH of 5 and a temperature of 20° C. The adjusted content of the adjusting tank 7 is the crude solution. The crude solution contains 40 kg of crystalline saccharin sodium per 100 kg of solution. The crude solution is circulated through extraction column 19 from bottom to top by means of metering pump 23 at a flow rate of 354 liters per hour and then passes in purified form into storage tank 2.

Storage tank 1 is filled with methylene chloride which has been previously purified by distillation. Methylene chloride from storage tank 1 has a temperature of 18° C. therein and is circulated through extraction column 19 from top to bottom by means of metering pump 24 at a flow rate of 885 liters per hour. It thus flows in the opposite direction to the solution of crude saccharin sodium and passes into evaporator 8. In the extraction column 19 the two counterflowing liquids mix in the manner of an emulsion under the action of sieve plates 18 and the pulsating pressure treatment by pulsator 17. Due to the different specific gravities the crude solution is separated from the emulsion at the top and the methylene chloride is separated therefrom at the bottom.

The crude solution which flows out of the top of the extraction column 19 passes into storage tank 2, from where the purified solution passes into evaporator 9. The distillate which consists of water and a small quantity of methylene chloride is condensed in condenser 16 and separated in separating tank 4. The distilled methylene chloride is returned to storage tank 1, while the water is supplied to the upstream connected saccharin sodium synthesis apparatus (not shown in the drawing).

The distillation residue from evaporator 9 passes into the crystallization tank 14 in which the pure saccharin sodium is crystallized and is then separated from the mother solution in separator 20. The mother solution is returned to the upstream connected saccharin sodium synthesis apparatus (not shown in the drawing) while the separated crystals pass into drier 21 in which they are dried and are then removed as end product.

The methylene chloride flowing out from the bottom of the extraction column 19 is purified by distillation in evaporator 8. The distillate is condensed in condenser 15, intermediately stored in storage tank 3 and then returned to storage tank 1. The distillation residue is discarded. 0.5% potassium carbonate is constantly fed into evaporator 8 as a function of the methylene chloride quantity to be evaporated in order to separate any acid impurities from the methylene chloride.

167 kg/hour of crystalline saccharin sodium are obtained.

The crude solution subjected to refining contained 50 ppm of impurities, mainly ortho-toluenesulphonamide. The pure saccharin sodium obtained as refined product contains less than 1 ppm of impurities.

As a modification of the above-described procedure, a small crude saccharin sodium solution charge may be purified in closed circuit. To this end, the crude solution which has passed through the extraction column 19 is returned to adjusting tank 7 from storage tank 2 via pipeline 27, shown by dotted lines. In said tank 7 the pH value and temperature are adjusted to the initial values described above. It is then again circulated through the extraction column 19 by metering pump 23 and flows in closed circuit until the desired purity level is obtained. The purified crude solution is then passed from storage tank 2 to evaporator 9. An intermittent operation of the circuit is possible but a continuous process is more advantageous. Only part of the purified crude solution is returned from storage tank 2 into adjusting tank 7 and the remainder is passed directly from storage tank 2 into evaporator 9. The deficit in adjusting tank 7 is made good by supplying further crude solution.

If the purified saccharin sodium obtained is not pure enough, the quantity of crude solution returned from storage tank 2 to adjusting tank 7 is increased at the expense of the throughput of the complete apparatus and vice versa.

The following example serves to describe the manner and process of making and using the invention and sets forth the best mode contemplated by the inventors of carrying out the invention, but is not to be construed as limiting.

EXAMPLE 1

A crude solution consists of 500 kg of saccharin sodium (crystal weight), contaminated by a total of 250 g of ortho-toluenesulphonamide dissolved in 750 kg of water. 1000 liters of methylene chloride are used as the solvent. The two charges are circulated for three hours countercurrently through the extraction column of an experimental plant. The experimental plant is constructed and operated in just the same way as the previously described industrial production plant, the only difference being that it is smaller in scale. When operating on an experimental basis, the crude solution is returned to the adjusting tank in accordance with dotted line 27 in the drawing of FIG. 1 and is then again circulated through the extraction column. The methylene chloride is distilled 4 to 5 times during the three hours and the crude solution passes through the extraction column 2 or 3 times during this period. At the end of the three hours the crude solution is collected in a storage tank corresponding to storage tank 2 in the drawing of FIG. 1 and then the purified crystalline saccharin sodium containing less than 1 ppm of ortho-toluenesulphonamide is obtained from the purified crude solution by distillation, crystallization and drying as described hereinbefore relative to the drawing of FIG. 1. The mother solution remaining after crystallization can be added to the next crude saccharin sodium solution charge intended for purification as described relative to the drawing of FIG. 1 hereinbefore.

What is claimed is:

1. A process for refining saccharin sodium soluted in an aqueous solution, said solution having been obtained by the process of Fahlberg-Rensen, and being contaminated with about 5000 ppm of o-toluenesulphonamide and containing 30 to 60 percent by crystal weight of saccharin sodium, which comprises;
    adjusting the contaminated solution to obtain a pH of from 4.5 to 6.0 and a temperature of from 15° to 22° C.;
    extracting the o-toluenesulphonamide with methylene chloride at a temperature of from 15° to 22° C. passed countercurrently to a flow of said contaminated solution and emulsified with the contaminated solution as they pass countercurrently by intermittently passing them through flow baffle plates, said flow of methylene chloride being substantially vertical in orientation whereby the methylene chloride is directed downwards;
    evaporating the methylene chloride residues from the extracted aqueous solution; and
    crystallizing the saccharin sodium from the evaporated solution;
    wherein the countercurrent extraction is continued until the saccharin sodium crystallizable from the aqueous solution has a content of less than 1 ppm o-toluenesulphonamide.

2. The method of claim 1 wherein said percent is 40 and said pH is from 5.0 to 5.5.

3. The process of claim 1 wherein the rate of flow of the methylene chloride during countercurrent extraction is two to three times that of the aqueous solution.

4. The process of claim 1 carried out continuously and wherein the aqueous solution and methylene chloride undergo countercurrent extraction in a closed circuit apparatus and during return flow the methylene chloride is purified by distillation.

5. A continuous process for refining saccharin sodium contaminated with o-toluenesulphonamide, which comprises;
    providing a 30 to 60 percent by crystal weight aqueous solution of saccharin sodium prepared by the process of Fahlberg-Remsen and contaminated with about 5000 ppm of o-toluenesulphonamide, having a pH of from 4.5 to 6.0;
    repeatedly extracting the o-toluenesulphonamide with methylene chloride passed counter-currently to a flow of said aqueous solution, at a temperature of from 15° to 22° C., said flow being substantially vertical in orientation and said methylene chloride and aqueous solution being emulsified as they pass countercurrently by passing them through flow baffle plates;
    distilling the methylene chloride between repeated extractions to separate extractants;
    evaporating the methylene chloride residues from the extracted aqueous solution; and
    crystallizing the saccharin sodium from the evaporated solution; and
    wherein the countercurrent extraction is continued until the saccharin sodium crystallizable from the aqueous solution has a content of less than 1 ppm o-toluenesulphonamide.

* * * * *